United States Patent
Mansour-Awad et al.

(10) Patent No.: US 11,471,473 B2
(45) Date of Patent: Oct. 18, 2022

(54) COMPOSITIONS AND METHODS FOR TREATING TRICHOMONAS

(71) Applicant: Chemistry RX, Folcroft, PA (US)

(72) Inventors: Amany Mansour-Awad, Philadelphia, PA (US); Lars Brichta, Brooklyn, NY (US)

(73) Assignee: Chemistry RX, Folcroft, PA (US)

( * ) Notice: Subject to any disclaimer, the term of this patent is extended or adjusted under 35 U.S.C. 154(b) by 0 days.

(21) Appl. No.: 16/456,532

(22) Filed: Jun. 28, 2019

(65) Prior Publication Data
US 2020/0000833 A1    Jan. 2, 2020

Related U.S. Application Data

(60) Provisional application No. 62/691,017, filed on Jun. 28, 2018.

(51) Int. Cl.
| | | |
|---|---|---|
| *A61K 31/7036* | (2006.01) | |
| *A61P 33/02* | (2006.01) | |
| *A61K 9/00* | (2006.01) | |
| *A61K 9/02* | (2006.01) | |
| *A61K 9/06* | (2006.01) | |
| *A61K 45/06* | (2006.01) | |

(52) U.S. Cl.
CPC ........ *A61K 31/7036* (2013.01); *A61K 9/0034* (2013.01); *A61K 9/02* (2013.01); *A61K 9/06* (2013.01); *A61P 33/02* (2018.01); *A61K 45/06* (2013.01)

(58) Field of Classification Search
CPC combination set(s) only.
See application file for complete search history.

(56) References Cited

FOREIGN PATENT DOCUMENTS

| | | | | |
|---|---|---|---|---|
| CN | 1372974 | * | 9/2002 | ............. A61K 38/43 |
| CN | 105726552 | * | 7/2006 | ......... A61K 31/7036 |
| RU | 2504396 | * | 1/2014 | ............. A61K 38/43 |

OTHER PUBLICATIONS

Tayal et al., "Paromomycin treatmentof recalcitrant Trichomonas vaginalis" International Journal of STD & AIDS vol. 21 pp. 217-218 (Year: 2010).*
English machine translation of CN 1372974, downloaded from https://worldwide.espacenet.com (Year: 2002).*
English machine translation of RU2504396, downloaded from https://worldwide.espacenet.com (Year: 2014).*
Cohelo et al., "Metronidazole resistant trichomoniasis successfully treated with paromomycin" Genitourinary Medicine vol. 73 pp. 397-398 (Year: 1997).*
Poppe et al., "Nitroimidazole-Resistant vaginal trichomoniasis treated with paromomycin" European Journal of Obstetrics and Gynecology and Reproductive Biology vol. 96 pp. 119-120 (Year: 2001).*
Nyirijesy et al., "Resistant Trichomoniasis: Successful Treatment With Combination Therapy" Sexually Transmitted Diseases vol. 38 No. 10 pp. 962-963 (Year: 2011).*
English machine translation of CN105726552, downloaded from worldwide.espacenet.com (Year: 2016).*
Nyirjesy et al., "Difficult-to-Treat Trichomoniasis: Results with Paromomycin Cream" Clinical Infectious Diseases vol. 26 pp. 986-988 (Year: 1998).*

* cited by examiner

*Primary Examiner* — Eric Olson
(74) *Attorney, Agent, or Firm* — Frost Brown Todd LLC

(57) ABSTRACT

Compositions and methods for treating Trichomoniasis using topically administered antibiotics such as aminoglycosides, including streptomycin, spectinomycin, kanamycin A, amikacin, tobramycin, dibekacin, gentamicin, sisomicin, netilmicin, neomycin B, neomycin C, neomycin E (paromomycin), and the like and combinations thereof.

19 Claims, No Drawings

COMPOSITIONS AND METHODS FOR TREATING TRICHOMONAS

CROSS-REFERENCE TO RELATED APPLICATIONS

This application claims priority from U.S. Provisional No. 62/691,017 entitled, "Compositions and Methods for Treating *Trichomonas*," filed on Jun. 28, 2018 the entity of which is hereby incorporated by reference.

GOVERNMENT INTERESTS

Not applicable
Parties to a Joint Research Agreement
Not applicable

Incorporation of Material on Compact Disc

Not applicable

BACKGROUND

Not applicable

Trichomoniasis is an infectious disease caused by the parasite *Trichomonas vaginalis* or *Trichomonas foetus* (*Tritrichomonas foetus*). Symptoms of trichomoniasis include itching in the genital area, a bad smelling thin vaginal discharge, burning with urination, and pain with sex. Trichomoniasis is often spread through vaginal, oral, or anal sex or genital touching.

Trichomoniasis is a common sexually transmitted disease that manifests in people, cattle, and cats. The disease is caused by the protozoan parasite *Trichomonas vaginalis* in humans and by *Trichomonas foetus* in cattle and cats. It is estimated that in the United States, 3.7 million people have the infection. In women, the most commonly infected part of the body is the genital tract including the vulva, vagina, cervix, and urethra. In men, the most commonly infected body part is the inside of the penis or urethra. During sexual intercourse, the parasite can travel from the urethra of the infected host to the vagina of the previously uninfected person or from the vagina of the infected host and into the penis of the previously uninfected person. Symptoms of the disease include vaginal discharge, itching, burning, redness or soreness of the genitals, urination discomfort, and vaginal discharge in women. Additionally, pregnant women who are infected are more likely to bear premature babies and to deliver babies with a low birth weight (less than 5.5 pounds. In men, symptoms include itching or irritation inside the penis, a burning after urination or ejaculation, and penile discharge. The condition can be cured with antibiotics, but due to antibiotic-resistant strains of trichomoniasis, novel methods of delivery and composition may be required in some cases.

SUMMARY OF THE INVENTION

Various embodiments are directed to methods and compositions for treating *Trichomonas* infection. Such compositions may include 0.25% (w/w) to about 30% (w/w) aminoglycoside antibiotic, and the methods may include topically, anally, or intravaginally administering to a subject in need of treatment a composition comprising 0.25% (w/w) to about 30% (w/w) aminoglycoside antibiotic. In certain embodiments, administering can be achieved using a suppository. In some embodiments, the aminoglycoside antibiotic may be streptomycin, spectinomycin, kanamycin A, amikacin, tobramycin, dibekacin, gentamicin, sisomicin, netilmicin, neomycin B, neomycin C, neomycin E (paromomycin), and the like and combinations thereof. In particular embodiments, the antibiotic may be tetracycline, lincomycin, clindamycin (7-chloro-7-deoxylincomycin), chloramphenicol, puromycin, and combinations thereof, and in certain embodiments, the antibiotic may be paromomycin.

In various embodiments, the compositions may be formulated in a form selected from the group consisting of creams, ointments, lotions, shampoos, liniments, foams, and soaps. In some embodiments, the composition may further include a debriding agent, such as, for example, papain, urea, balsam peru, castor oil, trypsin, chlorophyllin copper complex, collegenase, and the like and combinations thereof. In such embodiments, the debriding agent may have a concentration of about 0.25% (w/w) to about 20% (w/w) of the total composition. In some embodiments, the compositions may further include a base, such as, but not limited to, hydrophilic petrolatum, preserved water, sorbitan monooleate, benzalkonium chloride, mineral oil, plasticized base, glycerin, Versabase, preserved water, the like and combinations, analogs, and pharmaceutically acceptable salts thereof. In such embodiments, the base may have a concentration of about 65% (w/w) to about 90% (w/w) of the total composition. In some embodiments, the composition may further include an emulsifier or surfactant, and the emulsifier or surfactant may have a concentration of about 0.25% (w/w) to about 5% (w/w) of the total composition. In some embodiments, the composition may further include a humectant, such as, but not limited to, calamine, dodecylsulphate, sodium lauryl sulphate (SLS), a polyoxyethylene ester of polysorbitan, such as monooleate, monolaurate, monopalmitate, monostearate esters, esters of sorbitan, polyoxyethylenes ether, sodium dioctylsulphosuccinate (DOSS), lecithin, sodium docusate, and the like and combinations thereof. In such embodiments, the humectant may have a concentration of about 0.01% (w/w) to 5% (w/w) of the total composition.

Certain embodiments are directed to compositions such as those described above containing a ribosomal RNA binding compound having a concentration of about 0.25% (w/w) to about 30% (w/w) based on the total composition; and a debriding agent having a concentration of about 0.25% (w/w) to about 20% (w/w) topical debriding agent based on the total composition. In some embodiments, the compositions may include a base. In various embodiments, the ribosomal RNA binding compound may be, for example, streptomycin, spectinomycin, kanamycin A, amikacin, tobramycin, dibekacin, gentamicin, sisomicin, netilmicin, neomycin B, neomycin C, neomycin E, paromomycin, and the like and combinations thereof. In some embodiments, the debriding agent may be, for example, papain, urea, balsam peru, castor oil, trypsin, chlorophyllin copper complex, collegenase, and the like and combinations thereof.

DESCRIPTION OF THE DRAWINGS

Not applicable

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µl to 8 µl is stated, 2 µl, 3 µl, 4 µl, 5 µl, 6 µl, and 7 µl are also intended to be explicitly disclosed, as well as the range of values greater than or equal to 1 µl and the range of values less than or equal to 8 µl.

All percentages, parts and ratios are based upon the total weight of the topical compositions and all measurements made are at about 25° C., unless otherwise specified.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "administer," "administering" or "administration" as used herein refer to either directly administering a compound (also referred to as an agent of interest) or pharmaceutically acceptable salt of the compound (agent of interest) or a composition to a subject.

The term "carrier" as used herein encompasses carriers, excipients, and diluents, meaning a material, composition, or vehicle, such as a liquid or solid filler, diluent, excipient, solvent or encapsulating material involved in carrying or transporting a pharmaceutical, cosmetic or other agent across a tissue layer such as the stratum corneum or stratum spinosum.

The term "disorder" is used in this disclosure to mean, and is used interchangeably with the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject or enhance the growth, texture, appearance, color, sensation, or hydration of the intended tissue treatment area. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" or "cosmetically acceptable" is employed herein to refer to those agents of interest/compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, pharmaceutically acceptable means approved by a regulatory agency of the federal or a state government or listed in the U.S. Pharmacopeia or other generally recognized pharmacopeia for use in mammals (e.g. animals), and more particularly, in humans.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Non-limiting examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is an adult or child human.

The term "treating" is used herein, for instance, in reference to methods of treating a skin disorder or a systemic condition, and generally includes the administration of a compound or composition which reduces the frequency of, or delays the onset of, symptoms of a medical condition or enhance the growth, texture, appearance, color, sensation, or hydration of the intended tissue treatment area of the tissue surface in a subject relative to a subject not receiving the compound or composition. This can include reversing, reducing, or arresting the symptoms, clinical signs, and underlying pathology of a condition in a manner to improve or stabilize a subject's condition.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Various embodiments are directed to topical compositions containing one or more antibiotics for treating trichomoniasis. In certain embodiments, the antibiotic may be a ribosomal RNA-binding compound. Other embodiments are directed to methods for treating trichomoniasis that include administering a topical composition containing one or more antibiotics, antifungal agents, or combinations thereof to a subject in need of treatment, and in some embodiments, the methods may include the step of administering a topical composition containing one or more ribosomal RNA binding compound a subject in need of treatment. The compositions of such embodiments may be formulated as topical compositions and may provide reduction in trichomoniasis infection and rapid symptom relief.

The term "antibiotic" as used herein means any compound capable of reducing or eliminating infection. Antibiotics include, for example, antifungal agents, antimicrobial agents, antibacterial agents, and antiprotozoal agents.

The antibacterial, antimicrobial, and antifungal agent antibiotics encompassed by embodiments include, for example, amanfadine hydrochloride, amanfadine sulfate, amikacin, arnikacin sulfate, aminoglycosides, amoxicillin, ampicillin, ansamycins, bacitracin, beta-lactams, candicidin, capreomycin, carbenicillin, cephalexin, cephaloridine, cephalothin, cefazolin, cephapirin, cephradine, cephaloglycin, chloramphenicols, chlorhexidine, chlorhexidine gluconate, chlorhexidine hydrochloride, chloroxine, chlorquinaldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erythromycin stearate, farnesol, floxacillin, gentamicin, gentamicin sulfate, gramicidin, griseofulvin, haloprogin, haloquinol, hexachlorophene, iminocyldline, iodate, iodine, iodochlorhydroxyquin, kanamycin, kanamycin sulfate, lincomycin, lineomycin, lineomycin hydrochloride, macrolides, meclocycline, methacycline, methacycline hydrochloride, methenamine, methenamine hippurate, methenamine mandelate, methicillin, metronidazole, miconazole, miconazole hydrochloride, microcrystalline and nanocrystalline particles of silver, copper, zinc, mercury, tin, lead, bismuth, cadmium and chromium, minocycline, minocycline hydrochloride, mupirocin, nafcillin, neomycin, neomycin sulfate, netilmicin, netilmicin sulfate, nitrofurazone, norfloxacin, nystatin, octopirox, oleandomycin, orcephalosporins, oxacillin, oxytetracycline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, streptomycin, sulfonamide, tetracyclines, tetracycline, tobramycin, tobramycin sulfate, triclocarbon, triclosan, trimethoprim-sulfamethoxazole, tylosin, vancomycin, yrothricin and derivatives, esters, salts and mixtures thereof.

The antifungal agent antibiotics of embodiments include, for example, aminoquinuride (Surfen), acriflavine (Typaflavine), nystatin, miconazole (miconazole), terconazole (terconazole), isoconazole (isoconazole), fenticonazole (fenticonazole), fluconazole azole (fluconazole), ketoconazole (ketoconazole), clotrimazole (clotrimazole), butoconazole (butoconazole), econazole (econazole), metronidazole (metronidazole), clindamycin (clindamycin) and 5-fluorouracil (5-fluoracil), and such similar drugs and combinations thereof.

In particular embodiments, the antibiotic may be a ribosomal RNA binding compound. In some embodiments, the antibiotic may be an aminoglycoside antibiotic such as, for example, streptomycin, spectinomycin, kanamycin A, amikacin, amikan liposome, kanamycin, tobramycin, dibekacin, gentamicin, sisomicin, netilmicin, neomycin B, neomycin C, neomycin E (paromomycin), plazomicin, and the like and combinations thereof, and in certain embodiments, the antibiotic may be another ribosomal RNA inhibiting compound such as tetracycline, lincomycin, clindamycin (7-chloro-7-deoxylincomycin, chloramphenicol, puromycin, and the like and combinations thereof. In particular embodiments, the antibiotic may be paromomycin.

Aminoglycosides inhibit protein synthesis by binding to the cytosolic, membrane-associated bacterial ribosome. While specific steps in protein synthesis affected may vary somewhat between specific aminoglycoside agents, as can their affinity and degree of binding, aminoglycoside presence in the cytosol generally disturbs peptide elongation at the 30S ribosomal subunit, giving rise to inaccurate mRNA translation and therefore biosynthesis of proteins that are truncated, or bear altered amino acid compositions at particular points. Binding can also impair translational proofreading, leading to misreading of the RNA message, premature termination, or both, and so to inaccuracy of the translated protein product. The subset of aberrant proteins that are incorporated into the bacterial cell membrane may then lead to changes in its permeability. Inhibition of ribosomal translocation—i.e., movement of the peptidyl-tRNA from the A- to the P-site—has also been suggested as a mode of action. Any compound capable of acting as an aminoglycoside is encompassed by the invention and can be used as the antibiotic in the compounds and methods described herein.

The concentration of antibiotic in the composition of such embodiments can be up to about 30% (w/w), and in some embodiments, the concentration of antibiotic may be up to about 20% (w/w). For example, in some embodiments, the composition may include about 0.25% (w/w) to about 30% (w/w), about 0.5% (w/w) to about 20% (w/w), about 0.75% (w/w) to about 15% (w/w), about 1% (w/w) to about 15% (w/w), about 1% (w/w) to about 10% (w/w), or any range or individual concentration of antibiotic encompassed by these example ranges. In particular embodiments, the composition may include about 5% (w/w) to about 15% (w/w) streptomycin, spectinomycin, neomycin, paromomycin, or combinations thereof.

The compositions of various embodiments can be in any form, including topical formulations. Embodiments include, for example, one or more antibiotic containing creams, lotions, foams, liniments, balms, ointments, soaps, shampoos, and the like.

In some embodiments, the topical formulations can be in the form of a cream. Creams refer to semi-solid emulsions of oil and water in approximately equal proportions. They are divided into two types: oil-in-water (O/W) creams, composed of small droplets of oil dispersed in a continuous phase; and water-in-oil (W/O) creams, composed of small droplets of water dispersed in a continuous oily phase. Creams can provide a barrier to protect the skin. This may be a physical barrier or a chemical barrier as with UV-absorbing compounds. To aid in the retention of moisture (especially water-in-oil creams), creams are usually used for a variety of purposes including cleansing, emollient effects, and as a vehicle for drug substances such as local anesthetics, anti-inflammatories (NSAIDs or corticosteroids), hormones, antibiotics, antifungals or counter-irritants.

In some embodiments, the topical formulations can be in the form of a lotion. Lotions are low- to medium-viscosity topical preparation. Most lotions are oil-in-water emulsions containing an emulsifier such as cetyl alcohol to prevent separation of these two phases. Lotions can include fragrances, glycerol, petroleum jelly, dyes, preservatives, proteins and stabilizing agents.

In some embodiments, the topical formulations can be in the form of a foam. Pharmaceutical foams are pressurized dosage forms containing one or more active ingredients that, upon valve actuation, emit a fine dispersion of liquid and/or solid materials in a gaseous medium. Foam formulations are generally easier to apply, are less dense, and spread more easily than other topical dosage forms. Foams may be formulated in various ways to provide emollient or drying functions to the skin, depending on the formulation constituents. Accordingly, this delivery technology is a useful addition to the spectrum of formulations available for topical use.

In some embodiments, the topical formulations can be in the form of a liniment. Liniments or balms are topical formulations that are of a similar viscosity to lotions and less viscous than an ointment or cream. Liniments are generally applied with friction by rubbing the liniment into the skin. Liniments typically are formulated from alcohol, acetone, or similar quickly evaporating solvents and may contain counterirritant aromatic chemical compounds such as methyl salicylate, benzoin resin, or capsaicin.

In some embodiments, the topical formulations can be in the form of an ointment. Ointments are generally formulated using oils, waxes, alcohols, petroleum products, and other agents to prepare formulations with various viscosities and solvent properties. Commonly used formulations include oleaginous base (White Ointment), absorption base, W/O emulsion base (Cold Cream type base), O/W emulsion base (Hydrophilic Ointment), water soluble base, in addition to others. These preparations are used to dissolve or suspend substances or products with medicinal or cosmetic value.

In some embodiments, the formulations can be in the form of a soap, which are formulations that comprise a salt of a fatty acid. Soaps are mainly used as surfactants for washing, bathing, and cleaning, but they are also used in textile spinning and are important components of lubricants. Soaps for cleansing are usually obtained by treating vegetable or animal oils and fats with a strongly alkaline solution. Fats and oils are composed of triglycerides; three molecules of fatty acids are attached to a single molecule of glycerol. The alkaline solution, which is often called lye (although the term "lye soap" refers almost exclusively to soaps made with sodium hydroxide), is believed to promote a chemical reaction known as saponification. In saponification, the fats are first hydrolyzed into free fatty acids, which then combine with the alkali to form crude soap. Glycerol (glycerin) is usually liberated and is either left in or washed out and recovered as a useful byproduct, depending on the process employed.

In some embodiments, the topical formulations can be in the form of a shampoo, which is a hair care product used for the removal of oils, dirt, skin particles, dandruff, environmental pollutants, and other contaminant particles that gradually build up in hair. A goal may be to remove the unwanted build-up without stripping out so much sebum as to make hair unmanageable.

In some embodiments, the topical formulations can be in the form of a suppository. Suppository formulations can be prepared by admixing a therapeutically effective amount of an antibiotic as discussed above with a suppository base and forming suppositories from the admixture by any art recognized method of making suppositories. The suppository base is typically lipophilic and, in some embodiments, can be an aprotic lipophilic base such as a triglyceride lipophilic base or a paraffinic base comprising mixtures of hydrocarbons. The suppository base may have a melting temperature of from about 32° C. to 36° C. or a triglyceride mixture of fatty acids having a melting point range of from about 32° C. to 36° C. The mixture of hydrocarbons can preferably be a mixture of hard paraffin (about 50-60%) and liquid paraffin (about 40-50%) having a melting point range of about 32° C. to 36° C.

In certain embodiments, the suppository base may be a solid adjuvant mixture that is about 80% to about 90% by weight water-soluble, and in some embodiments, the suppository base may include solid polyethylene glycol, a liquid polyethylene gylcol that is soluble in the solid polyethylene glycol, solid oil-soluble surfactant, a water-soluble surfactant, and spermaceti. The physical properties of the various individual ingredients, by interaction, contribute to the properties of the formulated composition the characteristics which guarantee extrudability, water-dispersibility, and storage-stability. The amounts and proportions of the various ingredients of the base will vary with the amounts of the medicinal ingredients incorporated therein. In some embodiments, the solid polyethylene glycol may be about 23% to about 35% by weight of the total composition and the liquid polyethylene glycol may be about 10% to about 13% by weight of the total composition. The solid polyethylene glycol may have a molecular weight of about 4000 to about 6000, and the liquid polyethylene glycol may have a molecular weight of about 200 to about 600. The solid oil-soluble surfactant may be about 9% to about 11% by weight of the total composition and may be polyoxyethylene sorbitan monostearate (Tween 61) or polyoxyethylene sorbitan tristearate (Tween 65). The water-soluble surfactant may be about 4% to about 12% by weight of the total composition and can be an ethylene oxide-polyproplyene gylcol condensation product. Spermaceti can be about 26% to about 40% by weight of the total composition. A solid adjuvant can be beta lactose, sucrose, dextrose, sodium chloride, sodium sulfate, and the like and combinations thereof, and in some embodiments, the suppository formulation may include a starch such as corn starch, which can be mixed with small amounts of methylcellulose, guar gum, or purified wood cellulose.

Certain embodiments may include an emulsifier or surfactant such as, for example, cetyl alcohol, sorbitan laurate (SPAN® 20), sorbitan monopalmitate (SPAN® 40), sorbitan monostearate (SPAN® 60), sorbitan monooleate (SPAN® 80), polyoxyethylene sorbitan monolaureate (TWEEN® 20), polyoxyethylene sorbitan monopalmitate (TWEEN® 40), polysorbat 60 (TWEEN® 60), Polyethylene glycol sorbitan monolaurate (TWEEN® 80), Allyloxypolyethyleneglycol (APEG), Sodium dodecylbenzenesulfonate, Glycolic acid ethoxylate lauryl ether, Sodium alkylnapthalene sulfonate, Glycolic acid ethoxylate oleyl ether, Glycolic acid ethoxylate 4-tert-butylphenyl ether, and the like, derivatives of and combinations thereof. In such embodiments, the emulsifier or surfactant can be present in a concentration of about 0.25% (w/w) to about 5.0% (w/w), about 0.50% (w/w) to about 4% (w/w), about 0.75% (w/w) to about 3% (w/w), about 0.75% (w/w) to about 1% (w/w), or any range or individual concentration of solvent encompassed by these example ranges.

Example compositions may include various known components. For example, in some embodiments, the composition may include a solvent such as isopropyl alcohol, dipropylene glycol methyl-ether, butylated hydroxytoluene dipropylene glycol monomethyl-ether, 1-methoxy 2-propanol (glysolv PM/lcinol PM), Ethylene glycol monobutylether (butyl glyxolv/butyl icinol), Butyl di glysolv (butylicinol), Transcutol, propylene glycol (PG), N-methyl-2 pyrrolidone (NMP), methylene chloride, diethyl ether, ethanol, acetonitrile, ethyl acetate, benzyl alcohol, a combination of natural oil; ethylene glycol, propylene glycol, dimethyl polysiloxane (DMPX), oleic acid, caprylic acid, 1-octanol, ethanol (denatured or anhydrous), liposomal compositions, suitable plant oils, such as Aloe vera derivatives or sesame seed oil or derivatives thereof, acrylic polymers, rubber-based polymers, polysiloxane-based polymers, polyvinylpyrrolidone-based polymers, dimethylsulfoxide (DMSO), dimethylformamide (DMF), dimethylacetamide, N-methyl-2-pyrrolidone, hexamethylphosphoramide (HMPA), lecithin, Transfersomes® (bi-component vesicular aggregates), ethosomes, azone, castor oil derivatives, such as ethoxylated castor oil, jojoba oil derivatives, corn oil derivatives, emu oil derivatives, and the like and combinations thereof. The solvent can be present in a concentration of about 5.0% (w/w) to about 15.0% (w/w), about 6.0% (w/w) to about 10.0% (w/w), about 7.5% (w/w) to about 10.5% (w/w), about 8.0% (w/w) to about 10.0% (w/w), or any range or individual concentration of solvent encompassed by these example ranges.

In certain embodiments, the compositions may include a base such as, for example, white petrolatum, white petrolatum USP, mineral jelly, petroleum jelly, yellow petrolatum, yellow soft paraffin, white soft paraffin, fats, waxes, sterols, fat-soluble vitamins, monoglycerides, diglycerides, triglycerides, phospholipids, PCCA Plasticized base, Versabase, and the like and combinations thereof. In some embodiments, the base may be a liposomal base. Liposomal bases are an emulsion that includes a lipophilic component and an aqueous component that can be in the form of a lotion, a cream, a gel, or a paste. Examples of suitable liposomal bases include PCCA Lipoderm®, Lipoderm ActiveMax™, Anhydrous Lipoderm, and Lipoderm High Molecular Weight™ PCCA. Such liposomal base formulations can include, for example, about 60-80% wt/wt water combined with glycerin, $C_{12-15}$ alkyl benzoate, glyceryl stearate, dimethicone, cetearyl alcohol, cetearyl glucoside, polyacrylamide, cetyl alcohol, magnesium aluminum silicate, xanthan gum, aloe vera (aloe barbadensis), tocopheryl acetate (vitamin E acetate), prunus amygadalus amara (bitter almond) kernel oil, *Vitis vinifera* (Grape) seed extract, *Triticum vulgare* (wheat) germ oil, retinyl palmitate (vitamin A palmitate), ascorbyl palmitate (vitamin C palmitate), Pro-Lipo Multi-emulsion Liposomic System, tetrasodium EDTA, phenoxyethanol, sodium hydroxymethylglycinate and the like and combinations thereof.

The amount of base in the compositions of embodiments can vary and will depend on the amounts of the other components. More base can be added to compensate for smaller amounts of other components in the desired topical pharmaceutical formulation. In some embodiments, the base may be present in a concentration of about 65% (w/w) to about 99.75% (w/w) of the total composition, or any range or individual concentration known in the art.

In some embodiments, the compositions may include an antioxidant. Such antioxidant may be, for example, butylated hydroxytoluene, ascorbic acid, ascorbic palmitate, butylated hydroxyani sole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone, tocopherol, and the like and pharmaceutically acceptable salt or ester thereof or combinations thereof. The antioxidant can be present in a concentration of about 0.01% (w/w) to about 1% (w/w) of the total composition or any individual concentration encompassed by this example range.

In some embodiments, the composition may include an emulsifying agent including, for example, various monoglycerides, diglycerides, triglycerides, and blends thereof at a concentration of about 3% (w/w) to about 10% (w/w) of the total composition.

In some embodiments, the compositions may further include a humectant that provides soothing, smoothing, moisturizing, or protects the skin. The humectant is not limited and can be, for example, calamine, dodecylsulphate, sodium lauryl sulphate (SLS), a polyoxyethylene ester of polysorbitan, such as monooleate, monolaurate, monopalmitate, monostearate esters, esters of sorbitan, the polyoxyethylenes ethers, the sodium dioctylsulphosuccinate (DOSS), lecithin, and sodium docusate. The amount of humectant in such compositions may be about 0.01% (w/w) to 5% (w/w) of the total composition.

In some embodiments, the composition may further include an analgesic agent such as, for example, methyl salicylate, codeine, morphine, methadone, pethidine, buprenorphine, hydromorphine, levorphanol, oxycodone, fentanyl, a non-steroidal anti-inflammatory drug (NSAID), and the like and cobinations thereof. The amount of the analgesic agent such compositions may be about 0.01% (w/w) to 5% (w/w) of the total composition.

In some embodiments, the compositions may further include a debriding agent such as, for example, papain, urea, balsam peru, castor oil, trypsin, chlorophyllin copper complex, collagenase, and the like and combinations thereof. The concentration of debriding agent of such embodiments can be up to about 20% (w/w), and in some embodiments, the concentration of debriding agent may be up to about 15% (w/w). For example, in some embodiments, the composition may include about 0.25% (w/w) to about 20% (w/w), about 0.5% (w/w) to about 17.5% (w/w), about 0.75% (w/w) to about 15% (w/w), about 1% (w/w) to about 15% (w/w), about 1% (w/w) to about 12.5% (w/w), about 1% (w/w) to about 10% (w/w), or any range or individual concentration of topical debriding agent encompassed by these example ranges. In particular embodiments, the composition may include about 5% (w/w) to about 15% (w/w) urea.

In some embodiments, the compositions may further include a topical emollient such as, for example, urea, ammonium lactate, salicylic acid/urea, vitamins A, D, and E, ammonium lactate, pramoxine, vitamin A, vitamin D, ammonium lactate/urea, salicylic acid/urea, aloe vera, lanolin, and the like and combinations thereof. The amount of the emollient such compositions may be about 0.01% (w/w) to 5% (w/w) of the total composition.

Other embodiments of the invention include methods for treating *Trichomonas* by administering the compositions described above. The methods of various embodiments may include the steps of administering a composition of the various embodiments described above to the location of infection of subject in need of treatment. For example, the step of administering can include applying the compositions of embodiments to the genital area, pubis, vagina, anus, and combinations thereof of a patient in need of treatment. The step of administering can be carried out by various means. For example, administering can be accomplished by applying the composition to the skin of an infected subject, and in some embodiments, the skin may be massaged or rubbed to facilitate contacting of the antibiotic with the *Trichomonas* bacteria. In some embodiments, the step of administering can be carried out one, two, three, four, or more times per day, and administering can be carried out the prescribed number of times per day for one week to six months.

As is known in the art, certain means for administering may require the use of particular components of the formulation. Such components are described above and can be appropriately incorporated into the compositions. For example, certain embodiments include creams, lotions, and ointments including the antibiotics described above that are formulated to be administered to the genital area of a patient. Other embodiments include foams that can be applied using a pressurized container and compositions formulated for such delivery. Further embodiments include suppositories that are formulated as a solid or semisolid for administration to the anus or vagina of a patient.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

A paromomycin-containing composition was prepared and formulated for vaginal administration to Trichomoniasis patients. The paromomycin-containing formulation is provided in TABLE 1. TABLE 2 provides the formulation of the preserved water used in the paromomycin containing formulation.

TABLE 1

|  | Ex. 1 |
|---|---|
| Paromomycin | 20.95 g |
| Urea | 10.00 g |
| Hydrophilic Petrolatum | 54.39 g |
| Preserved Water | 13.66 g |
| Sorbitan Monoleate | 1 ml |

TABLE 2

Preparation of Preserved Water listed in TABLE 1

| Benzalkonium Chloride Solution 50% (v/v) | 0.2 mL |
|---|---|
| Purified Water | 1000 mL |

Example 2

Additional formulations of paromomycin containing compositions were created using various commercially available bases for vaginal administration to Trichomoniasis patients formulations. These formulations are provided in TABLE 3.

TABLE 3

|  | Ex. 2 | Ex. 3 | Ex. 4 |
|---|---|---|---|
| Paromomycin | 22.05 g | 7.35 g | 9.19 g |
| Mineral oil | 20 ml | | |
| PCCA Plasticized Base | 57.95 g | | |
| Glycerin (99.8%) | | 10 g | 12.5 g |
| Versabase | | 84.65 g | |
| Hydrophilic Petrolatum | | | 78.31 g |

The invention claimed is:

1. A method for treating *Trichomonas*, comprising administering to a subject in need of treatment a composition comprising a ribosomal RNA binding compound having a concentration of about 7.2% (w/w) to about 20% (w/w) and a debriding agent having a concentration of about 0.25% (w/w) to about 20% (w/w) topical debriding agent based on the total composition.

2. The method of claim 1, wherein the ribosomal RNA binding compound is selected from the group consisting of streptomycin, spectinomycin, kanamycin A, amikacin, tobramycin, dibekacin, gentamicin, sisomicin, netilmicin, neomycin B, neomycin C, neomycin E, paromomycin, and combinations thereof.

3. The method of claim 1, wherein the antibiotic is paromomycin.

4. The method of claim 1, wherein the debriding agent is selected from the group consisting of papain, urea, balsam peru, castor oil, trypsin, chlorophyllin copper complex, collagenase, and combinations thereof.

5. The method of claim 1, where the composition further comprises a base.

6. The method of claim 5, wherein the base is selected from the group consisting of hydrophilic petrolatum, preserved water, sorbitan monooleate, benzalkonium chloride, mineral oil, plasticized base, glycerin, preserved water, and combinations, analogs, and pharmaceutically acceptable salts thereof.

7. The method of claim 5, wherein the base has a concentration of about 65% (w/w) to about 90% (w/w) of the total composition.

8. The method of claim 1, wherein the composition further comprises an emulsifier or surfactant.

9. The method of claim 8, wherein the emulsifier or surfactant has a concentration of about 0.25% (w/w) to about 5% (w/w) of the total composition.

10. The method of claim 1, wherein the composition further comprises a humectant.

11. The method of claim 10, wherein the humectant is selected from the group consisting of calamine, dodecylsulphate, sodium lauryl sulphate (SLS), a polyoxyethylene ester of polysorbitan, sodium dioctylsulphosuccinate (DOSS), lecithin, sodium docusate, and combinations thereof.

12. The method of claim 10, wherein the humectant is a polyoxyethylene ester of a compound is selected from monooleate, monopalmitate, monostearate, sorbitan, and polyoxyethylene ether.

13. The method of claim 10, wherein the humectant has a concentration of about 0.01% (w/w) to 5% (w/w) of the total composition.

14. The method of claim 1, wherein administering is selected from the group consisting of intravaginal, anal, extravaginal administration, and combinations thereof.

15. The method of claim 1, wherein the composition is formulated in a form selected from the group consisting of creams, ointments, lotions, shampoos, liniments, foams, and soaps.

16. The method of claim 1, wherein the administering is achieved using a suppository.

17. A composition comprising:

A ribosomal RNA binding compound having a concentration of about 7.2% (w/w) to about 20% (w/w) based on the total composition; and A debriding agent having a concentration of about 0.25% (w/w) to about 20% (w/w) topical debriding agent based on the total composition.

18. The composition of claim 17, wherein the ribosomal RNA binding compound is selected from the group consisting of streptomycin, spectinomycin, kanamycin A, amikacin, tobramycin, dibekacin, gentamicin, sisomicin, netilmicin, neomycin B, neomycin C, neomycin E, paromomycin, and combinations thereof.

19. The composition of claim 17, wherein the debriding agent is selected from the group consisting of papain, urea, balsam peru, castor oil, trypsin, chlorophyllin copper complex, collagenase, and combinations thereof.

* * * * *